United States Patent [19]
Moi et al.

[11] Patent Number: 5,938,906
[45] Date of Patent: Aug. 17, 1999

[54] HORIZONTAL GEL ELECTROPHORESIS CASTING CASSETTE

[75] Inventors: Min Kar Moi, Escondido; Richard T. L. Chan, La Jolla; Robert G. Becker, Northridge, all of Calif.; Kelly C. Chalmers, Hartsville, S.C.

[73] Assignee: C.C. IMEX, San Diego, Calif.

[21] Appl. No.: 08/833,373

[22] Filed: Apr. 4, 1997

[51] Int. Cl.[6] .................................................. G01N 27/26
[52] U.S. Cl. ........................ 204/465; 204/466; 204/467; 204/616; 204/618; 204/619; 204/620
[58] Field of Search .................................... 204/616, 617, 204/618, 619, 620, 456, 465, 466, 467

[56] References Cited

U.S. PATENT DOCUMENTS

| | | |
|---|---|---|
| 4,795,541 | 1/1989 | Hurd et al. ........................ 204/299 R |
| 4,954,236 | 9/1990 | Kushner et al. ................... 204/299 R |
| 5,569,369 | 10/1996 | Leffler et al. ........................ 204/620 |

OTHER PUBLICATIONS

Page from Cosmo Bio Catalog.

*Primary Examiner*—David A. Redding
*Attorney, Agent, or Firm*—Townsend Townsend & Crew, LLP

[57] ABSTRACT

This invention provides a gel electrophoresis casting cassette for horizontal gel electrophoresis. The tray and lid of the cassette have locking means for securing the two parts to prevent damage to the slab gel and to create slab gels of uniform quality.

25 Claims, 4 Drawing Sheets

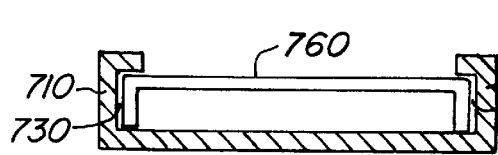
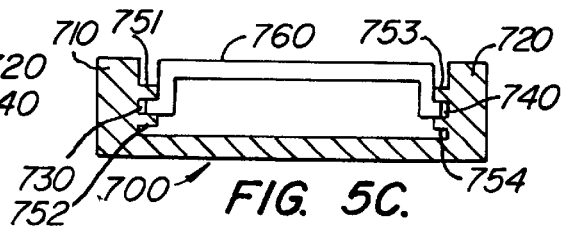
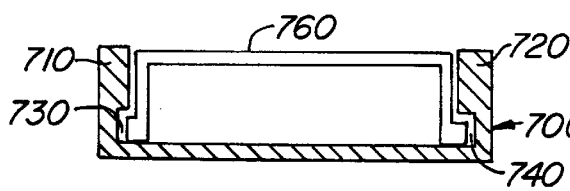
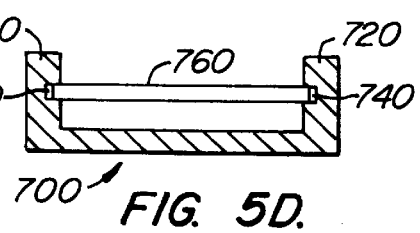
FIG. 5A.
FIG. 5B.
FIG. 5C.
FIG. 5D.
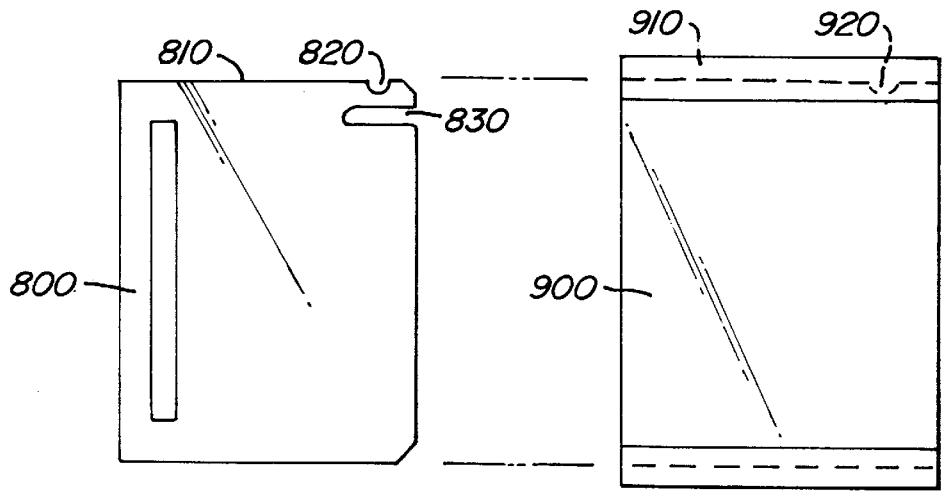
FIG. 6.
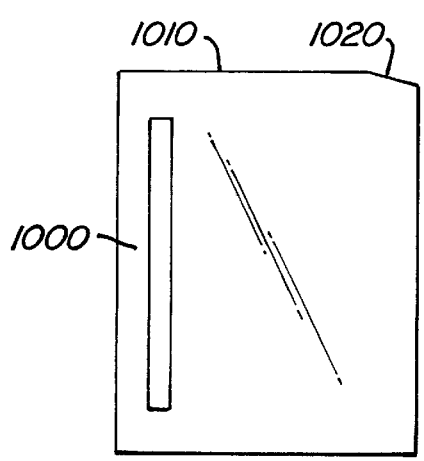
FIG. 7.

HORIZONTAL GEL ELECTROPHORESIS CASTING CASSETTE

BACKGROUND OF THE INVENTION

This invention relates to the field of apparatuses for gel electrophoresis.

Gel electrophoresis is a process in which charged analyte molecules move through a gel matrix under the force of an electrical field applied across the gel. After electrophoresis, the analytes can be fixed in the solid gel and identified, as in analytical gel electrophoresis. Also, the analyte can be eluted from the gel and isolated for further manipulation, as in preparative gel electrophoresis. Polyacrylamide and agarose are two of the most popular matrix materials for use with biomolecular analytes, such as proteins and nucleic acids.

The gel matrix usually takes the form of a slab or a tube. Slabs are run either horizontally or vertically. In either case sample wells are created in the gel in a line across the width of the gel and the voltage gradient is applied orthogonally to this line through the length of the slab gel.

Gels can be cast in an open four-walled compartment that holds the gel until it sets, or between two plates. Horizontal agarose slab gels generally are cast in an open four-walled compartment. Vertical and horizontal polyacrylamide slab gels generally are cast in a space formed between two plates. Casting plates are generally made of glass or plastic. In both horizontal and vertical gels, sample wells are created by dipping a comb into the gelling solution and allowing the gel to set around the comb.

Apparatuses for running horizontal gels generally include compartments that include electrodes and that hold electrophoresis buffer. The gel is placed between the two compartments so that the buffer contacts two ends of the gel and can impart a voltage gradient across the length of the gel. The electrodes are connected to a power supply. Such apparatuses are commercially available.

The relative movement of analytes in different parallel lanes of a slab gel depends primarily on the evenness of the voltage across the width of the gel at any point along the gel's length. The voltage at any point on the gel depends, in part, on the thickness of the gel.

Pre-cast, vertical polyacrylamide gels are now a marketplace staple. However, horizontal gels, especially those no more than about 3 mm thick and having an area of less than about 100 cm$^2$ have not yet found complete public acceptance. Gels may not have a uniform thickness and bubbles can form between the plates during the casting process. Also, during shipment, pre-cast horizontal polyacrylamide gels can tear or separate from the casting cassette. An example of an apparatus for horizontal gel electrophoresis is described in the Cosmo Bio catalog, number Mupid-2. The apparatus includes a horizontal electrophoresis cassette comprising two plates that loosely fit together and that have open front and back edges.

SUMMARY OF THE INVENTION

This invention provides a casting cassette for horizontal gel electrophoresis. The casting cassette comprises a tray and a lid. The tray comprises a substantially rectangular, flat floor having two opposing side walls perpendicular to the floor. The lid comprises a substantially rectangular, flat top having opposing side edges. The lid is adapted to fit along the side edges between the walls of the tray to create a slab-shaped space between the floor and top. The cassette further comprises locking means for preventing substantial sliding or lifting between the floor and the top. In one embodiment the shortest distance between a point on the top and the floor is uniform in any orthogonal edge-to-edge dimension. In another embodiment the top further comprises at least one slit for receiving at least one comb.

In one embodiment, the cassette includes two opposing flanges perpendicular to the top which support the lid on the tray and separate the top from the floor. The support can be by, for example, resting the flanges on the floor or locking between the flanges and the walls. The locking means include one or more protrusions on either the side walls or the flanges that fit with one or more indentations on the flanges or side walls, respectively.

The cassette of the invention, which includes locking means for substantially immobilizing the lid after the cassette is assembled, offers the following advantages. First, when gelling solution is poured between the plates, the lid does not float and rise, ensuring that the gel will have a uniform and pre-determined thickness. This improves uniformity of analyte movement in the gel. Second, transporting a pre-cast gel runs the risk of dislocating the gel from the cassette. The assembled, locked cassette protects the gel and decreases this risk. Third, assembled, locked cassettes have fewer moving parts and, therefore, are easier to work with. Therefore, they make it possible to cast gels in production scale for commercialization. Fourth, in the cassette of the invention, the front and back edges of the tray are exposed to the buffer containing the electrodes, allowing unimpeded current flow through the slab gel.

In another aspect, this invention provides a kit. The kit includes a cassette of the invention and one or more of the following items: a casting stand for the cassette; a comb adapted to fit into the slit; an electrophoresis unit having compartments with electrodes for holding buffer; a power supply for the electrophoresis unit; reagents for gel electrophoresis (gel, buffers, etc.); and instructions for using the kit.

In another aspect, this invention provides a method for casting a slab gel in a horizontal electrophoresis casting cassette. The cassette comprises (1) a tray comprising a substantially rectangular, flat floor having two opposing side walls perpendicular to the floor; (2) a lid comprising a substantially rectangular, flat top having opposite side edges, wherein the lid is adapted to fit along the side edges between the opposing walls of the tray to create a slab-shaped space between the floor and top; and (3) an open front edge and an open back edge. The method comprises the step of introducing gelling solution between the floor and the top wherein the cassette is tilted between the front edge and the back edge at an angle between about 0.5° and about 90°. In one embodiment of the method, the cassette is tilted at an angle between about 0.5° and about 15° with the front edge higher than the back edge, and the gelling solution is introduced into the open back edge.

BRIEF DESCRIPTION OF THE DRAWINGS

FIGS. 5a–5d show side views of casting cassettes with a groove or shelf in the tray into which a lid is slid.

FIG. 6 shows a sliding lid format of the cassette of the invention having a notch lock mechanism.

FIG. 7 shows a sliding lid format of the cassette of the invention having a friction fitting locking mechanism.

DETAILED DESCRIPTION OF THE INVENTION

Figure 1:
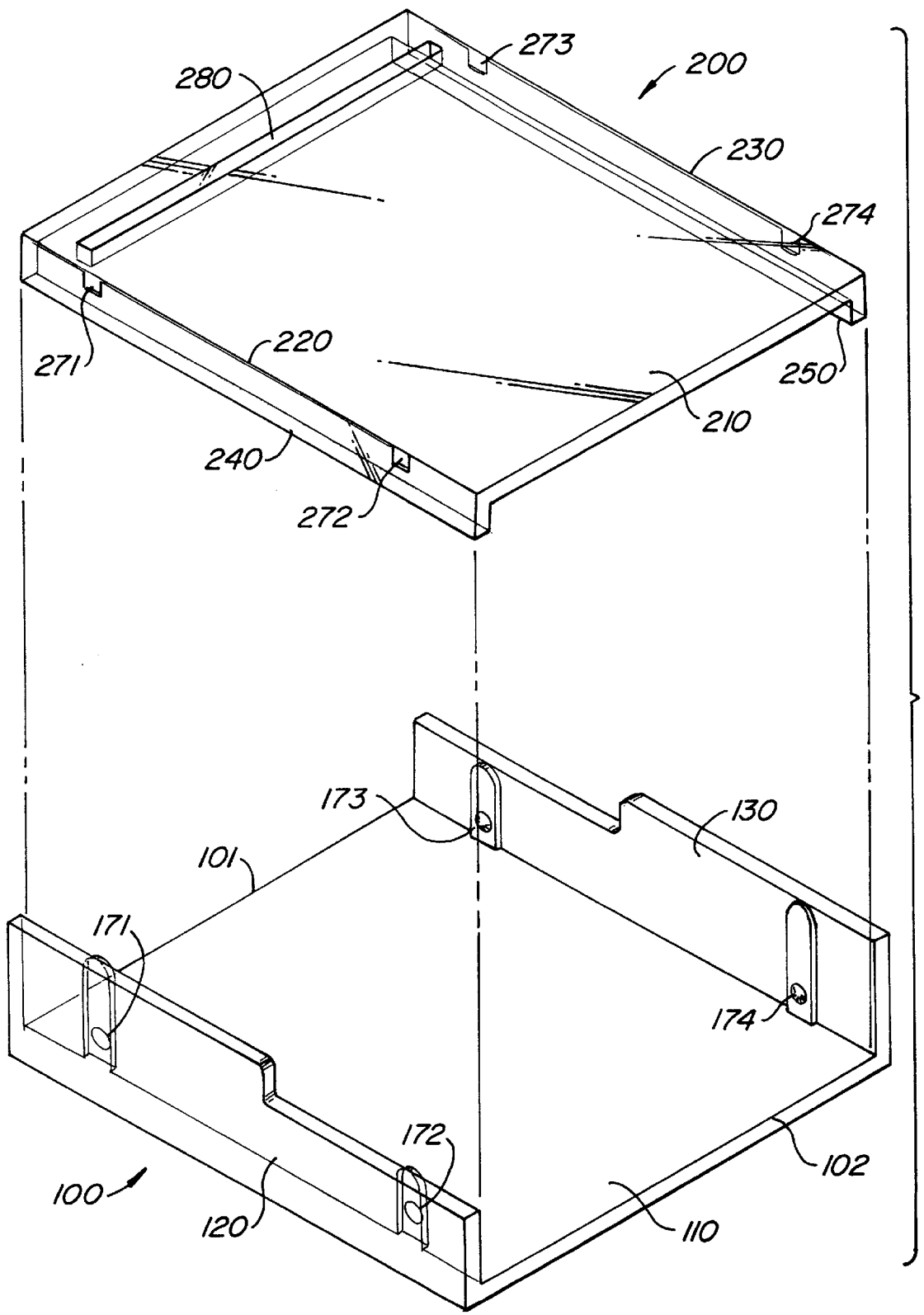
FIG. 1 shows an exploded view of the horizontal gel electrophoresis casting cassette of the invention.

Referring to FIG. 1, the cassette of the invention has tray 100 having a substantially rectangular, flat floor 110. Floor 110 has front edge 101 and back edge 102 that are to be substantially perpendicular to the flow of current when the cassette is in use. Floor 110 also has opposing side walls 120 and 130 that are substantially perpendicular to floor 110. In a cast gel, the floor acts as the substrate that supports the gel. Because current must pass through the gel, normally, front edge 101 and back edge 102 face the electrodes and will be open. Generally, the cathode is attached to the gel at front edge 101 and the anode is attached to the gel at back edge 102.

Figure 4:
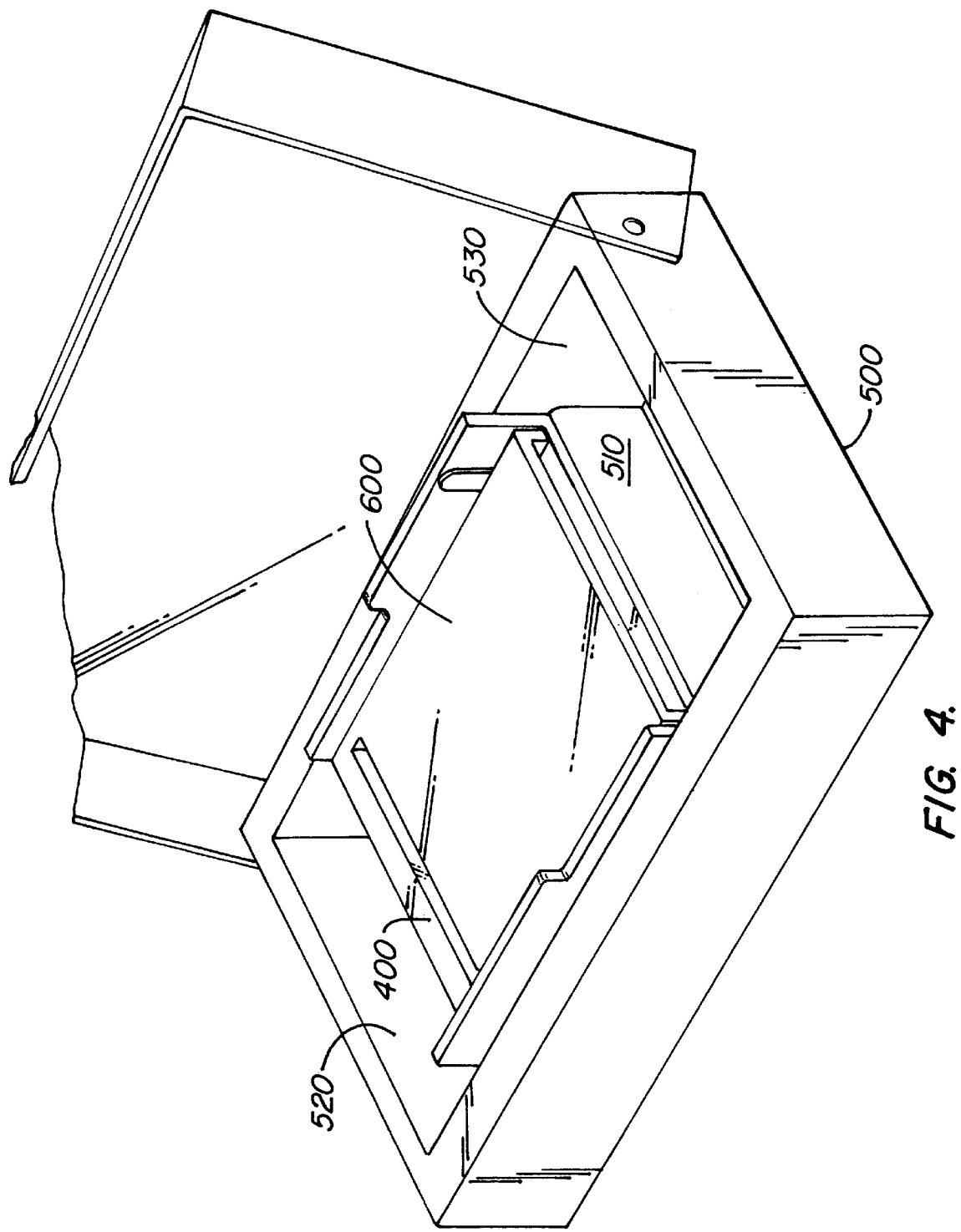
FIG. 4 shows a perspective of a casting cassette of the invention in an electrophoresis apparatus.

The floor had dimensions so as to fit inside a horizontal electrophoresis apparatus, to run the gel. FIG. 4 shows an assembled cassette in an electrophoresis apparatus in which the open ends of the cassette face the buffer compartments. The trays of the invention can be as small as about 2 cm×about 3 cm and as large as about 15 cm×about 15 cm. In one embodiment of the invention, the tray can fit an electrophoresis apparatus that accommodates gels about 11 cm wide and about 6 cm long. Pairs of trays also can be placed into the apparatus. In this case, the trays can be about 5.5 cm×about 6 cm.

The cassette also comprises a lid 200 that has a flat top 210 with substantially rectangular shape and opposing side edges 220 and 230. The lid is adapted to fit between opposing side walls 120 and 130 of tray 100 and to rest there so as to leave a space between top 210 and floor 110.

Figure 2:
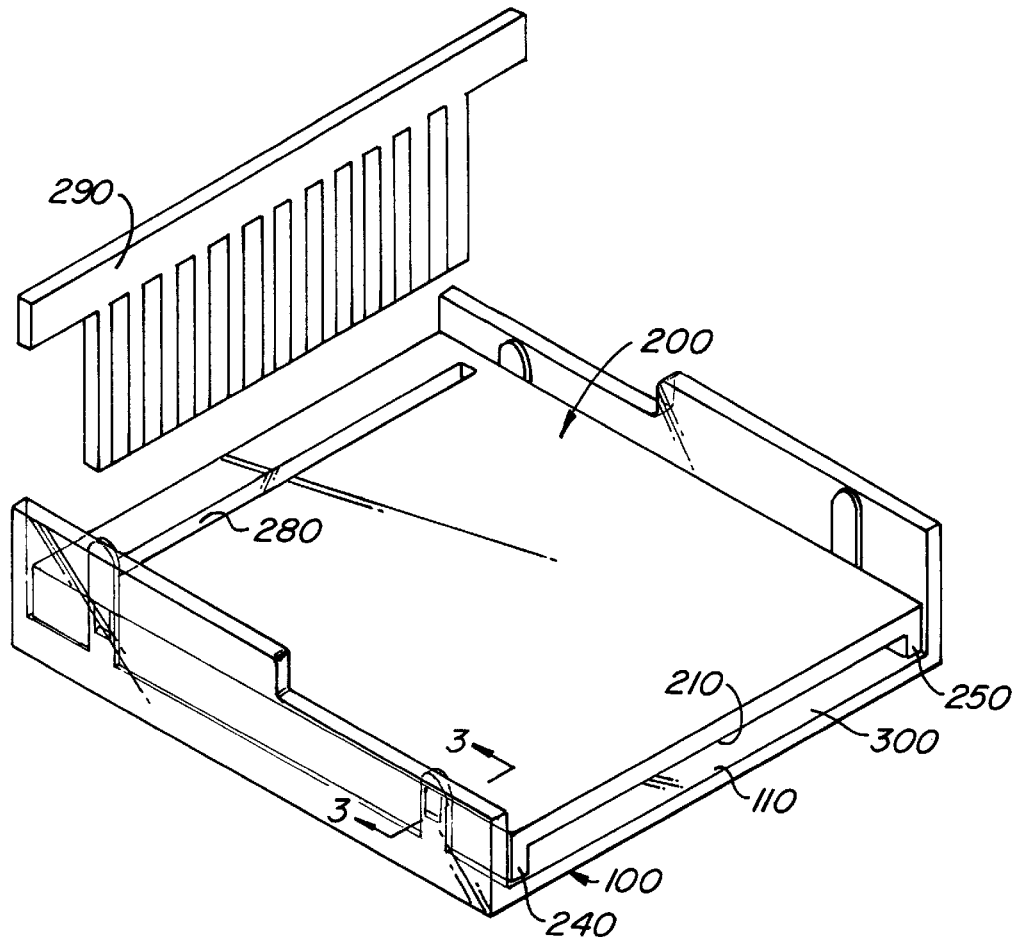
FIG. 2 shows a perspective view of an assembled casting cassette of the invention.

In the embodiment of FIGS. 1 and 2, creation of the space is accomplished by providing opposing flanges 240 and 250 extending substantially perpendicular to top 210. FIG. 2. shows an assembled cassette. When fitted with tray 100, lid 200 rests on floor 110 supported by flanges 240 and 250. Alternatively, the locking means may support the flanges. Flanges need not extend the length of edges 220 and 230, but can be, for example, notched. Alternatively, the flanges can be pegs so that the lid rests as a four-legged table on floor 110.

In another embodiment, depicted in FIG. 5, tray 700 can comprise substantially parallel grooves 730 and 740 in opposing walls 710 and 720. The grooves are adapted to fit the side edges of lid 760 so that the lid can slide or snap into the tray. In one embodiment, depicted in FIG. 5c, the grooves may be formed by two pairs of shelves 751, 752, 753 and 754. Including flexible side walls 710 and 720 aids in allowing top 760 to snap into tray 700.

In order to keep the voltage uniform across a line perpendicular to travel lanes, when lid 200 is fitted with tray 100 the shortest distance between a point on the top and the floor is uniform in any orthogonal edge-to-edge dimension. That is, along any line connecting and perpendicular to side edges 220 and 230 of the top and parallel to front edge 101 or back edge 102 (i.e., perpendicular to the flow of current), the distance between the floor and the top is the same. In one embodiment the shortest distance between a point on top 210 and floor 110 can be uniform throughout the cassette, so that the slab gel has uniform thickness throughout. In another embodiment, one may vary the voltage gradient in the direction of current flow by making the gel thicker at front edge or back edge. For example, in order to slow the movement of analytes toward the back edge of the gel, the gel at back edge 102 should be thicker than the gel at front edge 101.

The cassette of the invention further comprises locking means to prevent substantial vertical or horizontal play between the lid and the top. The locking means prevent the lid from floating when the gelling solution is poured between the floor and the top. They also prevent the lid from sliding across the tray and, possibly, separating the gel from the cassette. In certain embodiments, the locking means can be unlocked, so that the top is removably insertable into the tray. In another embodiment, the locking means permanently attach the lid to the tray.

Figure 3:
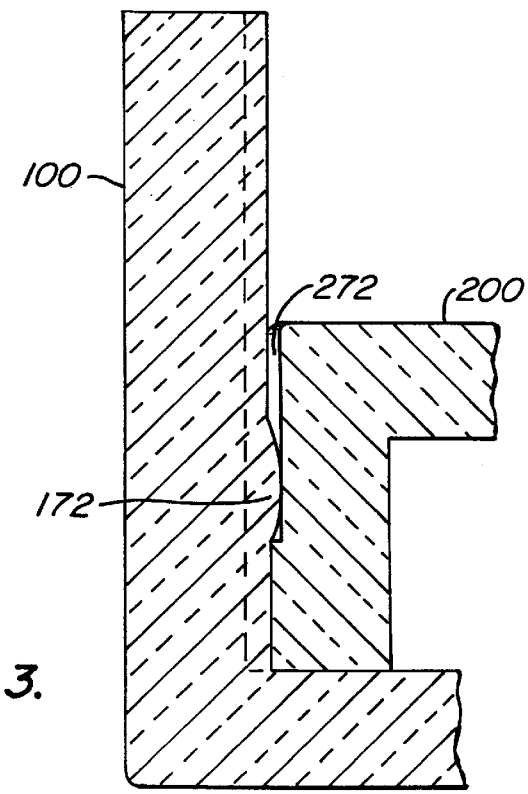
FIG. 3 shows cross-sectional view of a locking mechanism of a casting cassette of the invention.

In the embodiment depicted in FIG. 1, the locking means comprise protrusions, in this case bumps (i.e., raised spherical spots), 171, 172, 173 and 174 on walls 120 and 130 which oppose and engage indentations 271, 272, 273 and 274 on flanges 240 and 250. In this embodiment, the width of the lid is selected so that the indentation engages the protrusion. FIG. 3 shows protrusion 172 engaged with indentation 272 to prevent substantial horizontal or vertical movement of lid 200 with respect to tray 100. In an alternate version of this embodiment, the protrusions are positioned on the flanges and the indentations are positioned on the walls.

In another embodiment, the locking means is a friction fit between the flanges and opposing walls. However, care must be taken to ensure that this does not cause the top or bottom to bow. This would cause the thickness of the slab gel to be uneven across its width.

In another embodiment, the locking means comprise at least one pin or peg attached to the lid that insert with a friction fit into at least one hole cut into the floor of the tray. Alternatively the pin can extend from the floor and fit into a hole in the lid.

In an embodiment in which the lid slides into the grooves in the opposing walls (FIG. 5), the fit in the grooves prevents substantial vertical movement between the top and the floor. One means to prevent substantial horizontal movement is shown in FIG. 6. Lid 800 includes side edge 810 having notch 820. Tray 900 includes wall 910 having protrusion 920 that engages notch 820 with a snap lock when lid 900 is slid into a groove in tray 900. Notch 830 provides play in the locking mechanism.

In another sliding lid embodiment, shown in FIG. 7, lid 1000 has side edge 1010 with angled corner 1020. Tray 1100 includes wall 1110 having protrusion 1120 that engages angled corner 1020 with a friction fit when lid 1000 is slid into a groove in tray 1100.

In yet another embodiment, the locking means comprise an adhesive, such as tape, wrapped around the edge of the assembled cassette, glue or putty applied to the corners of the assembled cassette, thereby preventing substantial horizontal movement. It can attach, for example, the bottom of the flanges to the floor.

The assembled cassette generally includes means for creating sample wells in the gel. In one embodiment, this is achieved by including at least one slit 280 (FIGS. 1 and 2) in the lid into which at least one comb 290 fits. (See FIG. 2) At least one slit generally is positioned substantially closer to front edge 101 than to back edge 102. This allows the longest possible path through the gel for the sample to pass. In another embodiment, the lid includes a plurality of slits located, for example, two slots, one near the front edge and near the middle. In this way, two sets of samples can be run. The comb can have one or more teeth to create one or more sample wells.

In another embodiment in which the lid is removably insertable, the lid can include teeth in the top that extend down into the space where the gel will set. Removing the top exposes the wells for use.

In another embodiment, the length of the lid can be shorter than the length of the floor, thereby leaving an open space near one end of the cassette.

The lid and tray preferably comprise transparent plastic that can be coated. Most preferably, the plastic is acrylic. Other useful plastics for molding are well known in the art and include, for example, polystyrene, polycarbonate, polyester, and styrene acrylonitrile ("SAN") polymer. Agarose gels are poured hot. Therefore, cassettes for casting agarose gels normally are made of heat-resistant plastic, such as polycarbonate.

The lid and tray can be made by molding the plastic by means well known in the art. Plastic parts can be produced in a variety of methods including machining from solid blocks, casting by means of pouring molten material into formed cavities, or molding parts, where molten material is forced into cavities under pressure. Injection molding is a common way for producing parts with critical, closely held dimensions. Molten plastic is injected under pressure into metal molds or dies in a molding machine that heats the plastic, closes the molds to allow the molten material to be injected into single or multiple cavities, then opens to allow the completed parts to be extracted.

The lid and tray also can be made of glass. However, plastic is preferred for embodiments in which the locking mechanism involves engaging parts as in, e.g., snapping.

The cassettes of the invention are used to cast and run gels. In one embodiment, the assembled cassette is placed in a casting stand. The casting stand has walls defining a compartment into which gelling solution can be poured. The gelling solution, e.g., agarose or acrylamide, is poured into the casting stand and fills the slab-shaped space. About 9 ml to about 12 ml suffices to fill a cassette whose dimensions are about 5.5 cm×about 6 cm for a gel about 3 mm thick. Best results are obtained by pouring the gelling solution into a slightly tilted cassette. The cassette can be tilted, with the front edge higher, from about 0.5° to about 90° and, preferably, about 0.5° to about 15°. Liquid can be poured preferably at the back edge, but also at the front edge.

In another embodiment, rather than placing the cassette in a casting stand, an open end of the cassette is sealed with spring loaded covers, clamped plates or formfitting sleeves, or secured with tape.

Solidified gels can be used immediately, stored for later use, or transported. The locking mechanism aids in maintaining the integrity of the gel during transport, inhibiting the gel from sliding off the cassette or separating from it. Polyacrylamide and agarose gels are best stored in a sealed container at 4° C. and should be used within a few months.

Polymerized gels are used for electrophoresis in the usual manner. The cassette is placed on a platform with the open ends of the gel exposed to buffer which contains the electrodes. Sample is applied to the sample wells. An appropriate voltage (usually about 25 volts to about 200 volts) is applied for an appropriate time. Apparatuses for horizontal electrophoresis are commercially available. FIG. 4 depicts electrophoresis apparatus 500 having a platform 510 which supports cassette 600 and compartments 520 and 530 for buffer.

After electrophoresis is completed, the gel can be removed from the cassette for staining or isolation of the analyte by disassembling the cassette.

The cassette can be commercialized as a kit. The kit can include a comb and a casting stand for pouring gels. Alternatively, pre-cast gels can be assembled into kits with instructions for use. Also, cassettes can be included in kits containing a complete electrophoresis apparatus, with the cassettes fashioned to fit the apparatus.

The present invention provides novel cassettes for horizontal electrophoresis and methods for using them. While specific examples have been provided, the above description is illustrative and not restrictive. Many variations of the invention will become apparent to those skilled in the art upon review of this specification. The scope of the invention should, therefore, be determined not with reference to the above description, but instead should be determined with reference to the appended claims along with their full scope of equivalents.

What is claimed is:

1. A casting cassette for horizontal gel electrophoresis comprising:

a tray comprising a substantially rectangular, flat floor having two opposing side walls perpendicular to the floor;

a lid comprising a substantially rectangular, flat top having opposing side edges, wherein the lid is adapted to fit along the side edges between the walls of the tray to create a slab-shaped space between the floor and top; and locking means for preventing substantial sliding or lifting between the floor and the top, wherein the locking means comprises a protrusion that opposes and engages an indentation in either the lid or tray, a notch in the lid that engages a protrusion in the tray, or a friction fit between the lid and the tray.

2. The cassette of claim 1 wherein the shortest distance between a point on the top and the floor is uniform in any orthogonal edge-to-edge dimension.

3. The cassette of claim 2 wherein the top further comprises at least one slit for receiving at least one comb.

4. The cassette of claim 2 wherein the top further comprises two opposing flanges perpendicular to the top, wherein the flanges support the lid on the tray and separate the top from the floor.

5. The cassette of claim 2 wherein the walls comprise parallel grooves into which the lid slides or snaps.

6. The cassette of claim 2 wherein the slab-shaped space has a uniform thickness.

7. The cassette of claim 2 wherein the cassette comprises plastic.

8. The cassette of claim 2 comprising plastic wherein the top further comprises two opposing flanges perpendicular to the top wherein the flanges support the lid on the tray and separate the top from the floor; the locking means comprise a plurality of protrusions on the side walls and a plurality of indentations in the flanges, wherein each protrusion fits with an indentation; the rectangular floor has dimensions of about 5.5 cm×about 6 cm or about 11 cm×about 6 cm; the slab-shaped space has a uniform thickness of about 3 mm; and the top further comprises a slit for receiving a comb.

9. The cassette of claim 4 wherein the locking means comprise at least one protrusion in a wall or flange that fits with at least one indentation in a flange or wall, respectively.

10. The cassette of claim 4 wherein the locking means comprise a plurality of protrusions on the side walls and a plurality of indentations in the flanges, wherein each protrusion fits with an indentation.

11. The cassette of claim 4 wherein the floor comprises at least one pin or hole that, upon fitting the lid on the tray, opposes at least one hole or pin, respectively, in a flange, and the locking means comprise a friction fit between the at least one pin and the at least one hole.

12. The cassette of claim 4 wherein the rectangular floor has dimensions of about 5.5 cm×about 6 cm.

13. The cassette of claim 4 wherein the rectangular floor has dimensions of about 11 cm×about 6 cm.

14. The cassette of claim 5 wherein a side edge of the top comprises a notch and a wall of the tray comprises a protrusion that engages the notch when the lid is slid or snapped into the tray.

15. The cassette of claim 5 wherein a side edge of the top comprises an angled corner and a wall of the tray comprises a protrusion that engages the angled corner with a friction fit when the lid is slid into the tray.

16. The cassette of claim 6 wherein the thickness is about 3 mm.

17. The cassette of claim 7 wherein the plastic is acrylic.

18. The cassette of claim 7 wherein the plastic is selected from the group consisting of polystyrene, polycarbonate, polyester, and styrene acrylonitrile ("SAN") polymer.

19. A kit comprising:
  (1) casting cassette for horizontal gel electrophoresis comprising:
    a tray comprising a substantially rectangular, flat floor having two opposing side walls perpendicular to the floor;
    a lid comprising a substantially rectangular, flat top having opposing side edges, wherein the lid is adapted to fit along the side edges between the walls of the tray to create a slab-shaped space between the floor and top; and
    locking means for preventing substantial sliding or lifting between the floor and the top;
  (2) a casting stand comprising a compartment for receiving the cassette; and
  (3) a comb adapted to fit into the slit.

20. The kit of claim 19 wherein the top further comprises two opposing flanges perpendicular to the top, wherein the flanges support the lid on the tray and separate the top from the floor and wherein the locking means comprise one or more protrusions on the side walls and one or more indentations on the flanges wherein each protrusion fits with an indentation; and wherein the shortest distance between a point on the top and the floor is uniform in any orthogonal edge-to-edge dimension.

21. The kit of claim 20 further comprising an electrophoresis unit and power supply.

22. The kit of claim 20 further comprising reagents for gel electrophoresis.

23. The kit of claim 20 further comprising instructions for using the kit.

24. A method for casting a slab gel in a horizontal electrophoresis casting cassette, the cassette comprising:
  tray comprising a substantially rectangular, flat floor having two opposing side walls perpendicular to the floor; and
  a lid comprising a substantially rectangular, flat top having opposing side edges, wherein the lid is adapted to fit along the side edges between the walls of the tray to create a slab-shaped space between the floor and top; and
  an open front edge and an open back edge;
  the method comprising the step of introducing gelling solution between the floor and the top wherein the cassette is tilted between the front edge and the back edge at an angle between about 0.5° and about 90° whereby the front edge is tilted higher than the back edge, and wherein the gelling solution is introduced into the open back edge.

25. The method of claim 24 wherein the cassette is tilted at an angle between about 0.5° and about 15° with the front edge higher than the back edge, and the gelling solution is introduced into the open back edge.

* * * * *